(12) United States Patent
Simon

(10) Patent No.: US 8,880,175 B2
(45) Date of Patent: Nov. 4, 2014

(54) SYSTEMS AND METHODS FOR SELECTIVELY APPLYING ELECTRICAL ENERGY TO TISSUE

(71) Applicant: ElectroCore, LLC, Morris Plains, NJ (US)

(72) Inventor: Bruce J. Simon, Mountain Lakes, NJ (US)

(73) Assignee: Electrocore, LLC, Basking Ridge, NJ (US)

( * ) Notice: Subject to any disclaimer, the term of this patent is extended or adjusted under 35 U.S.C. 154(b) by 0 days.

(21) Appl. No.: 13/937,099

(22) Filed: Jul. 8, 2013

(65) Prior Publication Data

US 2013/0304169 A1   Nov. 14, 2013

Related U.S. Application Data

(62) Division of application No. 12/469,397, filed on May 20, 2009, now Pat. No. 8,483,832.

(51) Int. Cl.
*A61N 1/36* (2006.01)
*A61N 1/04* (2006.01)

(52) U.S. Cl.
CPC .......... *A61N 1/0456* (2013.01); *A61N 1/36017* (2013.01); *A61N 1/36007* (2013.01); *A61N 1/3601* (2013.01); *A61N 1/36117* (2013.01); *A61N 1/36114* (2013.01)
USPC .................................. 607/42; 607/2; 607/44

(58) Field of Classification Search
None
See application file for complete search history.

(56) References Cited

U.S. PATENT DOCUMENTS

| | | | |
|---|---|---|---|
| 4,196,737 A | 4/1980 | Bevilacqua |
| 5,458,141 A | 10/1995 | Neil |
| 5,983,131 A | 11/1999 | Weaver et al. |
| 6,341,236 B1 | 1/2002 | Osorio et al. |
| 6,463,327 B1 | 10/2002 | Lurie et al. |
| 6,587,719 B1 | 7/2003 | Barrett et al. |
| 6,610,713 B2 | 8/2003 | Tracey |
| 7,797,041 B2 | 9/2010 | Libbus et al. |
| 2002/0099417 A1 | 7/2002 | Naritoku et al. |
| 2002/0183237 A1 | 12/2002 | Puskas |
| 2004/0243182 A1 | 12/2004 | Cohen et al. |
| 2004/0249416 A1 | 12/2004 | Yun et al. |

(Continued)

FOREIGN PATENT DOCUMENTS

| | | |
|---|---|---|
| WO | WO 93/01862 | 2/1993 |
| WO | WO 2009/021080 | 2/2009 |
| WO | WO 2009/135693 | 11/2009 |

OTHER PUBLICATIONS

Greicius et al., Functional connectivity in the resting brain: A network analysis of the default mode hypothesis, PNAS, Jan. 2003, vol. 100, No. 1, pp. 253-258.

(Continued)

*Primary Examiner* — Paula J Stice
(74) *Attorney, Agent, or Firm* — Dentons US LLP

(57) ABSTRACT

Systems and devices for selectively applying electrical energy to a target region beneath a skin surface of a patient involve applying an electrical impulse to one or more electrodes on a skin surface of the patient to modulate one or more nerves at the target region, where the impulse is substantially blocked at nerves located between the target region and the skin surface such that only the nerves at the target region are modulated by the electrical impulse.

11 Claims, 6 Drawing Sheets

(56) References Cited

U.S. PATENT DOCUMENTS

| | | |
|---|---|---|
| 2005/0021092 A1 | 1/2005 | Yun et al. |
| 2005/0065574 A1 | 3/2005 | Rezai |
| 2005/0137644 A1 | 6/2005 | Bojeva et al. |
| 2006/0074284 A1 | 4/2006 | Juola et al. |
| 2006/0100668 A1 | 5/2006 | Ben-David et al. |
| 2006/0100671 A1 | 5/2006 | Ridder |
| 2006/0173510 A1 | 8/2006 | Besio et al. |
| 2006/0178703 A1 | 8/2006 | Huston et al. |
| 2007/0027496 A1 | 2/2007 | Parnis et al. |
| 2007/0123952 A1 | 5/2007 | Strother et al. |
| 2007/0142886 A1 | 6/2007 | Fischell et al. |
| 2007/0150006 A1 | 6/2007 | Libbus et al. |
| 2007/0276449 A1 | 11/2007 | Gunter et al. |
| 2008/0021512 A1 | 1/2008 | Knudson et al. |
| 2008/0027513 A1 | 1/2008 | Carbunaru |
| 2008/0045776 A1 | 2/2008 | Fischell et al. |
| 2008/0051852 A1 | 2/2008 | Dietrich et al. |
| 2008/0177190 A1 | 7/2008 | Libbus et al. |
| 2008/0208266 A1* | 8/2008 | Lesser et al. ................ 607/2 |
| 2008/0306325 A1 | 12/2008 | Burnett et al. |
| 2009/0157149 A1 | 6/2009 | Wahlgren et al. |
| 2009/0187231 A1* | 7/2009 | Errico et al. ................ 607/42 |
| 2009/0234419 A1 | 9/2009 | Maschino et al. |
| 2009/0259274 A1* | 10/2009 | Simon et al. ................ 607/40 |
| 2009/0287035 A1 | 11/2009 | Dietrich et al. |
| 2010/0286553 A1 | 11/2010 | Feler et al. |
| 2011/0046432 A1 | 2/2011 | Simon et al. |
| 2011/0152967 A1 | 6/2011 | Simon et al. |
| 2011/0213295 A1 | 9/2011 | Henley et al. |
| 2011/0224749 A1 | 9/2011 | Ben-David et al. |
| 2011/0230701 A1 | 9/2011 | Simon et al. |
| 2012/0029601 A1 | 2/2012 | Simon et al. |
| 2012/0283697 A1 | 11/2012 | Kim et al. |
| 2012/0303080 A1 | 11/2012 | Ben-David et al. |

OTHER PUBLICATIONS

Heneka et al., Locus ceruleus controls Alzheimer's disease pathology by modulating microglial functions through norepinephrine, PNAS, Mar. 2010, vol. 107, No. 13, pp. 6058-6063.

Lee et al., Clustering of Resting State Networks, PLoS One, Jul. 2012, vol. 7, Issue 7, pp. 1-12.

International Search Report and Written Opinion dated Mar. 26, 2008 in related PCT Application No. PCT/US2006/042752 filed Nov. 1, 2006 (7 pages).

International Search Report and Written Opinion dated Sep. 17, 2007 in related PCT Application No. PCT/US2006/042828 filed Nov. 2, 2006 (5 pages).

International Search Report and Written Opinion dated May 8, 2007 in related PCT Application No. PCT/US2006/042823 filed Nov. 2, 2006 (5 pages).

International Search Report and Written Opinion dated Dec. 22, 2011 in related PCT Application No. PCT/US2011/049844 filed Aug. 31, 2011 (9 pages).

International Search Report and Written Opinion dated Apr. 30, 2013 in related PCT Application No. PCT/US2013/023014 filed Jan. 24, 2013 (7 pages).

International Search Report and Written Opinion dated Dec. 11, 2013 in related PCT Application No. PCT/US2013/058079 filed Sep. 4, 2013 (8 pages).

International Search Report and Written Opinion dated Jan. 29, 2014 in related PCT Application No. PCT/US2013/068804 filed Nov. 6, 2013 (10 pages).

* cited by examiner

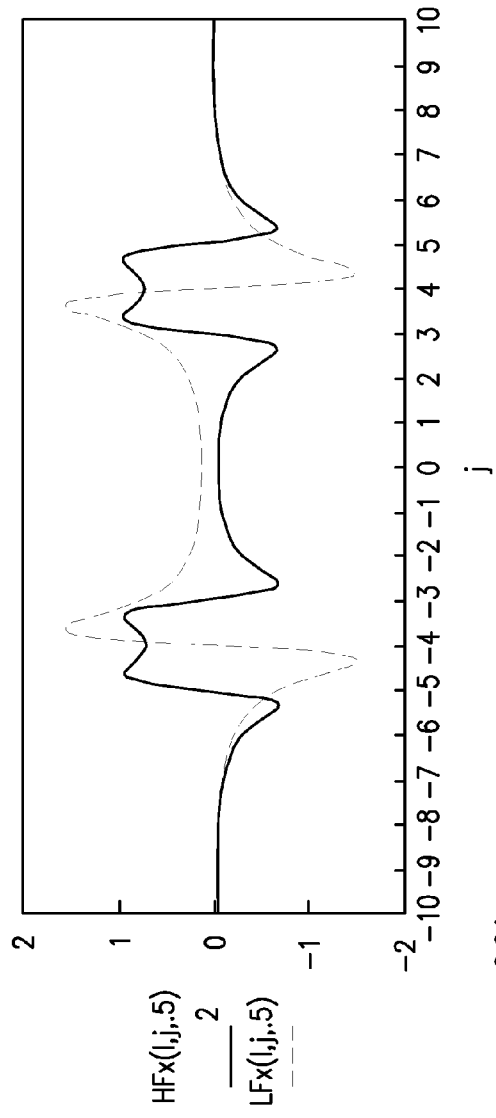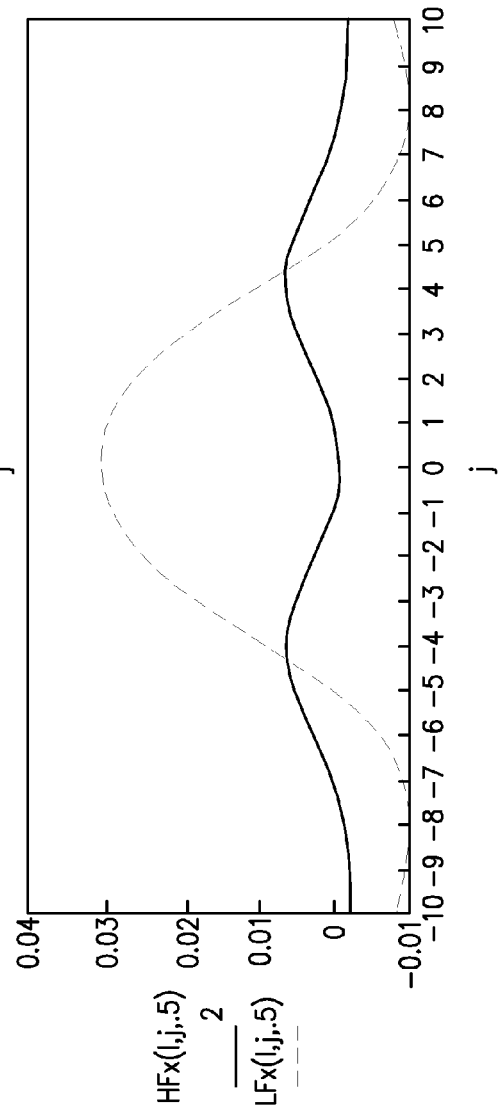

SYSTEMS AND METHODS FOR SELECTIVELY APPLYING ELECTRICAL ENERGY TO TISSUE

CROSS REFERENCE TO RELATED APPLICATIONS

This present application is a Divisional of U.S. patent application Ser. No. 12/469,397 filed 20 May 2009 now U.S. Pat. No. 8,483,832, which is incorporated herein by reference in its entirety.

BACKGROUND OF THE INVENTION

The present invention relates to the field of delivery of electrical impulses (and/or fields) to bodily tissues for therapeutic purposes, and more specifically to devices, systems and method for selectively applying electrical energy to treat the immediate symptoms of certain conditions, such as hypotension, shock, the arrest of intestinal peristalsis and bronchial constriction resulting from pathologies such as anaphylactic shock, asthma and COPD.

Asthma, and other airway occluding disorders resulting from inflammatory responses and inflammation-mediated bronchoconstriction, affects an estimated eight to thirteen million adults and children in the United States. A significant subclass of asthmatics suffers from severe asthma. An estimated 5,000 persons die every year in the United States as a result of asthma attacks. Up to twenty percent of the populations of some countries are affected by asthma, estimated at more than a hundred million people worldwide. Asthma's associated morbidity and mortality are rising in most countries despite increasing use of anti-asthma drugs.

Asthma is characterized as a chronic inflammatory condition of the airways. Typical symptoms are coughing, wheezing, tightness of the chest and shortness of breath. Asthma is a result of increased sensitivity to foreign bodies such as pollen, dust mites and cigarette smoke. The body, in effect, overreacts to the presence of these foreign bodies in the airways. As part of the asthmatic reaction, an increase in mucous production is often triggered, exacerbating airway restriction. Smooth muscle surrounding the airways goes into spasm, resulting in constriction of airways. The airways also become inflamed. Over time, this inflammation can lead to scarring of the airways and a further reduction in airflow. This inflammation leads to the airways becoming more irritable, which may cause an increase in coughing and increased susceptibility to asthma episodes.

Two medicinal strategies exist for treating this problem for patients with asthma. The condition is typically managed by means of inhaled medications that are taken after the onset of symptoms, or by injected and/or oral medication that are taken chronically. The medications typically fall into two categories; those that treat the inflammation, and those that treat the smooth muscle constriction. The first is to provide anti-inflammatory medications, like steroids, to treat the airway tissue, reducing its tendency to over-release of the molecules that mediate the inflammatory process. The second strategy is to provide a smooth muscle relaxant (e.g. an anticholinergic) to reduce the ability of the muscles to constrict.

It has been highly preferred that patients rely on avoidance of triggers and anti-inflammatory medications, rather than on the bronchodilators as their first line of treatment. For some patients, however, these medications, and even the bronchodilators are insufficient to stop the constriction of their bronchial passages, and more than five thousand people suffocate and die every year as a result of asthma attacks.

Anaphylaxis likely ranks among the other airway occluding disorders of this type as the most deadly, claiming many deaths in the United States every year. Anaphylaxis (the most severe form of which is anaphylactic shock) is a severe and rapid systemic allergic reaction to an allergen. Minute amounts of allergens may cause a life-threatening anaphylactic reaction. Anaphylaxis may occur after ingestion, inhalation, skin contact or injection of an allergen. Anaphylactic shock usually results in death in minutes if untreated. Anaphylactic shock is a life-threatening medical emergency because of rapid constriction of the airway. Brain damage sets in quickly without oxygen.

The triggers for these fatal reactions range from foods (nuts and shellfish), to insect stings (bees), to medication (radio contrasts and antibiotics). It is estimated 1.3 to 13 million people in the United States are allergic to venom associated with insect bites; 27 million are allergic to antibiotics; and 5-8 million suffer food allergies. All of these individuals are at risk of anaphylactic shock from exposure to any of the foregoing allergens. In addition, anaphylactic shock can be brought on by exercise. Yet all are mediated by a series of hypersensitivity responses that result in uncontrollable airway occlusion driven by smooth muscle constriction, and dramatic hypotension that leads to shock. Cardiovascular failure, multiple organ ischemia, and asphyxiation are the most dangerous consequences of anaphylaxis.

Anaphylactic shock requires advanced medical care immediately. Current emergency measures include rescue breathing; administration of epinephrine; and/or intubation if possible. Rescue breathing may be hindered by the closing airway but can help if the victim stops breathing on his own. Clinical treatment typically consists of antihistamines (which inhibit the effects of histamine at histamine receptors) which are usually not sufficient in anaphylaxis, and high doses of intravenous corticosteroids. Hypotension is treated with intravenous fluids and sometimes vasoconstrictor drugs. For bronchospasm, bronchodilator drugs such as salbutamol are employed.

Given the common mediators of both asthmatic and anaphylactic bronchoconstriction, it is not surprising that asthma sufferers are at a particular risk for anaphylaxis. Still, estimates place the numbers of people who are susceptible to such responses at more than 40 million in the United States alone.

Tragically, many of these patients are fully aware of the severity of their condition, and die while struggling in vain to manage the attack medically. Many of these incidents occur in hospitals or in ambulances, in the presence of highly trained medical personnel who are powerless to break the cycle of inflammation and bronchoconstriction (and life-threatening hypotension in the case of anaphylaxis) affecting their patient.

Unfortunately, prompt medical attention for anaphylactic shock and asthma are not always available. For example, epinephrine is not always available for immediate injection. Even in cases where medication and attention is available, life saving measures are often frustrated because of the nature of the symptoms. Constriction of the airways frustrates resuscitation efforts, and intubation may be impossible because of swelling of tissues.

Typically, the severity and rapid onset of anaphylactic reactions does not render the pathology amenable to chronic treatment, but requires more immediately acting medications. Among the most popular medications for treating anaphylaxis is epinephrine, commonly marketed in so-called "Epipen" formulations and administering devices, which potential sufferers carry with them at all times. In addition to serving as an extreme bronchodilator, epinephrine raises the patient's heart rate dramatically in order to offset the hypotension that accompanies many reactions. This cardiovascular stress can result in tachycardia, heart attacks and strokes.

Chronic obstructive pulmonary disease (COPD) is a major cause of disability, and is the fourth leading cause of death in the United States. More than 12 million people are currently diagnosed with COPD. An additional 12 million likely have the disease and don't even know it. COPD is a progressive disease that makes it hard for the patient to breathe. COPD can cause coughing that produces large amounts of mucus, wheezing, shortness of breath, chest tightness and other symptoms. Cigarette smoking is the leading cause of COPD, although long-term exposure to other lung irritants, such as air pollution, chemical fumes or dust may also contribute to COPD. In COPD, less air flows in and out of the bronchial airways for a variety of reasons, including loss of elasticity in the airways and/or air sacs, inflammation and/or destruction of the walls between many of the air sacs and overproduction of mucus within the airways.

The term COPD includes two primary conditions: emphysema and chronic obstructive bronchitis. In emphysema, the walls between many of the air sacs are damaged, causing them to lose their shape and become floppy. This damage also can destroy the walls of the air sacs, leading to fewer and larger air sacs instead of many tiny ones. In chronic obstructive bronchitis, the patient suffers from permanently irritated and inflamed bronchial tissue that is slowly and progressively dying. This causes the lining to thicken and form thick mucus, making it hard to breathe. Many of these patients also experience periodic episodes of acute airway reactivity (i.e., acute exacerbations), wherein the smooth muscle surrounding the airways goes into spasm, resulting in further constriction and inflammation of the airways. Acute exacerbations occur, on average, between two and three times a year in patients with moderate to severe COPD and are the most common cause of hospitalization in these patients (mortality rates are 11%). Frequent acute exacerbations of COPD cause lung function to deteriorate quickly, and patients never recover to the condition they were in before the last exacerbation. Similar to asthma, current medical management of these acute exacerbations is often insufficient.

Unlike cardiac arrhythmias, which can be treated chronically with pacemaker technology, or in emergent situations with equipment like defibrillators (implantable and external), there is virtually no commercially available medical equipment that can chronically reduce the baseline sensitivity of the muscle tissue in the airways to reduce the predisposition to asthma attacks, reduce the symptoms of COPD or to break the cycle of bronchial constriction associated with an acute asthma attack or anaphylaxis.

Blood pressure exceeding normal values is called arterial hypertension. Hypertension by itself is only rarely an acute problem, with the seldom exception of hypertensive crisis, such as severe hypertension with acute impairment of an organ system (especially the central nervous system, cardiovascular system and/or the renal system) and the possibility of irreversible organ-damage. However, because of its long-term indirect effects (and also as an indicator of other problems) it is a serious worry to physicians diagnosing it. Persistent hypertension is one of the risk factors for strokes, heart attacks, heart failure, arterial aneurysms, and is the second leading cause of chronic renal failure after diabetes mellitus.

All level of blood pressure puts mechanical stress on the arterial walls. Higher pressures increase heart workload and progression of unhealthy tissue growth (atheroma) that develops within the walls of arteries. The higher the pressure, the more stress that is present and the more atheroma tend to progress and the heart muscle tends to thicken, enlarge and become weaker over time.

Blood pressure that is too low is known as hypotension. Low blood pressure may be a sign of severe disease and requires more urgent medical attention. When blood pressure and blood flow is very low, the perfusion of the brain may be critically decreased (i.e., the blood supply is not sufficient), causing lightheadedness, dizziness, weakness and fainting.

Sometimes the blood pressure drops significantly when a patient stands up from sitting. This is known as orthostatic hypotension; gravity reduces the rate of blood return from the body veins below the heart back to the heart, thus reducing stroke volume and cardiac output. When people are healthy, they quickly constrict the veins below the heart and increase their heart rate to minimize and compensate for the gravity effect. This is done at a subconscious level via the autonomic nervous system. The system usually requires a few seconds to fully adjust and if the compensations are too slow or inadequate, the individual will suffer reduced blood flow to the brain, dizziness and potential blackout. Increases in G-loading, such as routinely experienced by supersonic jet pilots "pulling Gs", greatly increases this effect. Repositioning the body perpendicular to gravity largely eliminates the problem.

Hypotension often accompanies and complicates many other systemic health problems, such as anaphylaxis and sepsis, leading to anaphylactic shock and septic shock, making it more difficult to address the underlying health problem. For example, U.S. Patent Application Number 20050065553, Ben Ezra, et al., titled, "Applications of vagal stimulation," which is incorporated in its entirety by reference, proposes to a method to treat a patient's sepsis by applying an appropriately configured current to the vagus nerve. However, when accompanied with refractory arterial hypotension, sepsis becomes septic shock.

Septic shock is a serious medical condition causing such effects as multiple organ failure and death in response to infection and sepsis. Its most common victims are children and the elderly, as their immune systems cannot cope with the infection as well as those of full-grown adults, as well as immunocompromised individuals. The mortality rate from septic shock is approximately 50%. Other various shock conditions include: systemic inflammatory response syndrome, toxic shock syndrome, adrenal insufficiency, and anaphylaxis.

There are two types of intestinal obstructions, mechanical and non-mechanical. Mechanical obstructions occur because the bowel is physically blocked and its contents can not pass the point of the obstruction. This happens when the bowel twists on itself (volvulus) or as the result of hernias, impacted feces, abnormal tissue growth, or the presence of foreign bodies in the intestines. Ileus is a partial or complete non-mechanical blockage of the small and/or large intestine. Unlike mechanical obstruction, non-mechanical obstruction, Ileus or paralytic Ileus, occurs because peristalsis stops. Peristalsis is the rhythmic contraction that moves material through the bowel.

Ileus may be associated with an infection of the membrane lining the abdomen, such as intraperitoneal or retroperitoneal infection, which is one of the major causes of bowel obstruction in infants and children. Ileus may be produced by mesenteric ischemia, by arterial or venous injury, by retroperitoneal or intra-abdominal hematomas, after intra-abdominal surgery, in association with renal or thoracic disease, or by metabolic disturbances (e.g., hypokalemia).

Gastric and colonic motility disturbances after abdominal surgery are largely a result of abdominal manipulation. The small bowel is largely unaffected, and motility and absorption are normal within a few hours after operation. Stomach emptying is usually impaired for about twenty four hours, but the colon may remain inert for about forty-eight to seventy-two hours (and in some cases 4-7 days). These findings may be confirmed by daily plain x-rays of the abdomen taken postoperatively; they show gas accumulating in the colon but not in the small bowel. Activity tends to return to the cecum before it returns to the sigmoid. Accumulation of gas in the small bowel implies that a complication (e.g., obstruction, peritonitis) has developed.

Symptoms and signs of Ileus include abdominal distention, vomiting, obstipation, and cramps. Auscultation usually reveals a silent abdomen or minimal peristalsis. X-rays may show gaseous distention of isolated segments of both small and large bowel. At times, the major distention may be in the colon. When a doctor listens with a stethoscope to the abdomen there will be few or no bowel sounds, indicating that the intestine has stopped functioning. Ileus can be confirmed by x rays of the abdomen, computed tomography scans (CT scans), or ultrasound. It may be necessary to do more invasive tests, such as a barium enema or upper GI series, if the obstruction is mechanical. Blood tests also are useful in diagnosing paralytic Ileus.

Conventionally, patients may be treated with supervised bed rest in a hospital, and bowel rest—where nothing is taken by mouth and patients are fed intravenously or through the use of a nasogastric tube. In some cases, continuous nasogastric suction may be employed, in which a tube inserted through the nose, down the throat, and into the stomach. A similar tube can be inserted in the intestine. The contents are then suctioned out. In some cases, especially where there is a mechanical obstruction, surgery may be necessary. Intravenous fluids and electrolytes may be administered, and a minimal amount of sedatives. An adequate serum K level (>4 mEq/L [>4 mmol/L]) is usually important. Sometimes colonic Ileus can be relieved by colonoscopic decompression. Cecostomy is rarely required.

Drug therapies that promote intestinal motility (ability of the intestine to move spontaneously), such as cisapride and vasopressin (Pitressin), are sometimes prescribed. Some reported opiate therapies (such as alvimopan) are directed to inhibiting sympathetic nerve transmission to improve intestinal peristalsis.

Unfortunately, many lengthy post operative stays in the hospital are associated with Ileus, where the patient simply cannot be discharged until his bowels move. The clinical consequences of postoperative Ileus can be profound. Patients with Ileus are immobilized, have discomfort and pain, and are at increased risk for pulmonary complications. Ileus also enhances catabolism because of poor nutrition. It has been reported in the 1990's that, overall, Ileus prolongs hospital stays, costing $750 million annually in the United States. Thus, it stands to reason that the healthcare costs associated with Ileus over a decade later are much higher. The relatively high medical costs associated with such post operative hospital stays are clearly undesirable, not to mention patient discomfort, and other complications. There are not, however, any commercially available medical equipment that can treat Ileus.

Accordingly, there is a need in the art for new products and methods for acutely treating the immediate symptoms of certain conditions, such as hypotension, shock, the arrest of intestinal peristalsis and bronchial constriction resulting from pathologies such as anaphylactic shock, asthma and COPD.

SUMMARY OF THE INVENTION

The present invention provides systems, apparatus and methods for selectively applying electrical energy to body tissue. In a method according to the present invention, an electric impulse is applied to a first target region located beneath an outer skin surface of a patient. The electric impulse is substantially blocked, minimized or inhibited in a second target region located between the outer skin surface and the target region. A key advantage of the prevent invention is that the device may be used to stimulate, inhibit or otherwise modulate tissue, such as nerves, located beneath a patient's outer skin surface, while substantially blocking or minimizing any stimulation of the superficial nerves on or directly under the skin surface. This allows an electrical impulse to be applied at a sufficiently high amplitude to effectively treat nerves located deep beneath the skin surface without causing pain to the patient around the superficial sensory nerves.

The electric impulse is preferably applied by contacting at least one activating electrode to the outer skin surface and delivering an electrical signal sufficient to stimulate one or more nerves in the first target region. The signal is preferably blocked or inhibited in the second target region by delivering a second electrical impulse or to deactivate the nerves in the second target region. In one embodiment, the second electrical impulse is applied to the activating electrode simultaneously with the first impulse. In other embodiments, the second electrical impulse is applied by contacting at least one deactivating electrode to the outer skin surface and delivering an electrical signal to the electrode to deactivate one or more nerves in the second target region.

The first electrical impulse or treatment impulse will typically have an amplitude that is sufficient to reach the target region, preferably at least 2 volts and typically between 20-200 volts. The frequency and pulse width of the treatment impulse will vary depending on the desired treatment. In some embodiments, the frequency may be about 1 Hz or greater, such as between about 15-50 Hz and the pulse width may be 20 uS or greater such as about 20 uS to about 1000 uS.

The second electrical impulse or blocking impulse will typically have an amplitude that is less than the treatment impulse, typically between about 5-50 volts, preferably less than about 2 volts. The blocking impulse will have a frequency that is substantially higher than the treatment impulse, typically at least 2000 Hz and preferably between about 4000 Hz and 5000 Hz and a pulse width that is less than 100 uS.

In another aspect of the invention, a device is provided having an activating device configured for applying an electric treatment impulse to a first target region of the tissue in a patient and a deactivating device positioned in close proximity to the activating device configured to inhibit or block the electric impulse in a second target region of the tissue. In this manner, the device may be used to selectively apply electrical energy to a specific target region within a patient's body, while preventing the electrical energy from substantially affecting non-target regions that may be adjacent to, or in close proximity with, the target tissue.

In one embodiment, the activating device is a source of electrical energy, such as a pulse generator, coupled to at least one activating electrode for delivering an electrical treatment impulse that is sufficient to stimulate, inhibit or otherwise modulate tissue, such as nerves. The deactivating device is a source of electrical energy coupled to at least one deactivating electrode for delivering a second electrical blocking impulse that is sufficient to deactivate or depolarize nerves such that the nerves enter an extended refractory period where they are unable to fire. The sources of electrical energy may be two separate sources, such as two pulse generators, or a single source configured to apply two different signals to the activating and deactivating electrodes.

In a preferred embodiment, the activating device includes first and second contact electrodes having opposite polarities and configured for contacting an outer skin surface of the patient. In alternative embodiments, the activating device may comprise a single "active" electrode configured for applying the electrical impulse and a second "return" electrode located elsewhere on the patient's body (i.e., a monopolar configuration). The deactivating device preferably includes two pairs of surface contact electrodes configured for placement on either side of each of the activating electrodes. It will be recognized by those skilled in the art that other configurations are possible, such as a monopolar configuration for both activating and deactivating devices, a bipolar deactivating device and a monopolar deactivating device and the like.

In a preferred embodiment, the first and second activating electrodes are designed to deliver the treatment impulse to a target region located at a specific distance from the outer skin surface. In one embodiment, the activating electrodes are spaced from each other a selected distance and an appropriate waveform is delivered to the electrodes to ensure that the signal reaches the target region with sufficient energy to stimulate, inhibit or modulate one or more nerves at the target region. In preferred embodiments, the electrodes are spaced from each other in such a manner as to deliver the electrical impulse a distance greater than 1 cm from the skin surface, preferably greater than 2 cm and, in some embodiments, greater than 5 cm below the skin surface. In alternative embodiments, the electrodes are sized and shaped to selectively deliver the treatment impulse to the target region underneath the skin surface.

The deactivating electrodes are preferably spaced on either side of each of the activating electrodes a selected distance to ensure that the blocking signal reaches a second target region between the first target region and the outer skin surface. The size and location of the second target region will largely depend on the location of the first target region. For example, if the first target region is about 5 cm below the surface of the patient's skin, the deactivating electrodes will be spaced on either side of each of the activating electrodes such that nerves between the skin surface and up to about 5 cm below are deactivated or depolarized and thus blocked or at least inhibited from stimulation by the activating electrodes. This allows treatment of deeper tissue without stimulation of shallow nerves, which would otherwise cause the patient pain.

In another embodiment, the activating and deactivating electrodes are configured in a concentric circle design. In this embodiment, the deactivating electrode comprises a substantially annular electrode surrounding each activating electrode. The annular deactivating electrode is spaced from the activating electrode a suitable distance to substantially block the signal from the activating electrode at a superficial target region as discussed above.

The present invention also provides a system for delivering electrical impulses to a target region within a patient that comprises a source of electrical energy, such as a pulse generator, coupled to activating and deactivating electrodes. The electrical energy source is configured to apply a treatment impulse to the activating electrodes that will stimulate one or more nerves at a certain depth under the outer skin surface of the patient. In preferred embodiments, the treatment impulse is sufficient to stimulate one or more nerves to increase their activity levels. The electrical energy is also configured to apply a second electrical blocking impulse to the deactivating electrodes that will cause one or more nerves to depolarize for an extended period of time so that the nerves become fatigued or exhausted and unable to polarize while the second electrical impulse is applied. Thus, these nerves become substantially impervious to the first electrical impulse.

In certain embodiments, the present invention contemplates an electrical impulse delivery device that delivers one or more electrical impulses to at least one selected region within a patient, such as the carotid sheath or the epidural space within the spinal cord. In this embodiment, the device is positioned in contact with an outer skin surface of the patient in a region selected to deliver the electrical impulse to the selected region to modulate, stimulate, inhibit or block electrical signals in nerves located in or around the carotid sheath or spinal cord, such as parasympathetic nerves, sympathetic nerves and/or the spinal levels from T5 to L2.

In an exemplary embodiment, the present invention is designed to modulate one or more nerves to reduce the magnitude of constriction of bronchial smooth muscle of the mammal that may be associated with asthma, COPD, anaphylaxis or other airway disorders. In other embodiments, the electrical signal is adapted to reduce, stimulate, inhibit or block electrical signals in nerves, such as the vagus nerve, sympathetic nerves or the spinal cord, to either reduce or increase a blood pressure of the mammal or to treat other ailments, such as orthostatic hypotension, hypotension associated with sepsis or anaphylaxis, post-operative ileus, hypertension, asthma, COPD, sepsis, epilepsy, depression, obesity and any other ailment affected by nerve transmissions.

Other aspects, features, advantages, etc. will become apparent to one skilled in the art when the description of the invention herein is taken in conjunction with the accompanying drawings.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims.

FIG. 5 illustrates an exemplary electric field profile of activating and deactivating signals as a function of distance along the nerve axis at a depth of 0.5 cm from the surface of the skin in accordance with an embodiment of the present invention; and FIG. 6 illustrates an exemplary electric field profile of activating and deactivating signals as a function of distance along the nerve axis at a depth of 5.0 cm from the surface of the skin in accordance with an embodiment of the present invention;

DETAILED DESCRIPTION OF THE PREFERRED EMBODIMENTS

Figure 1:
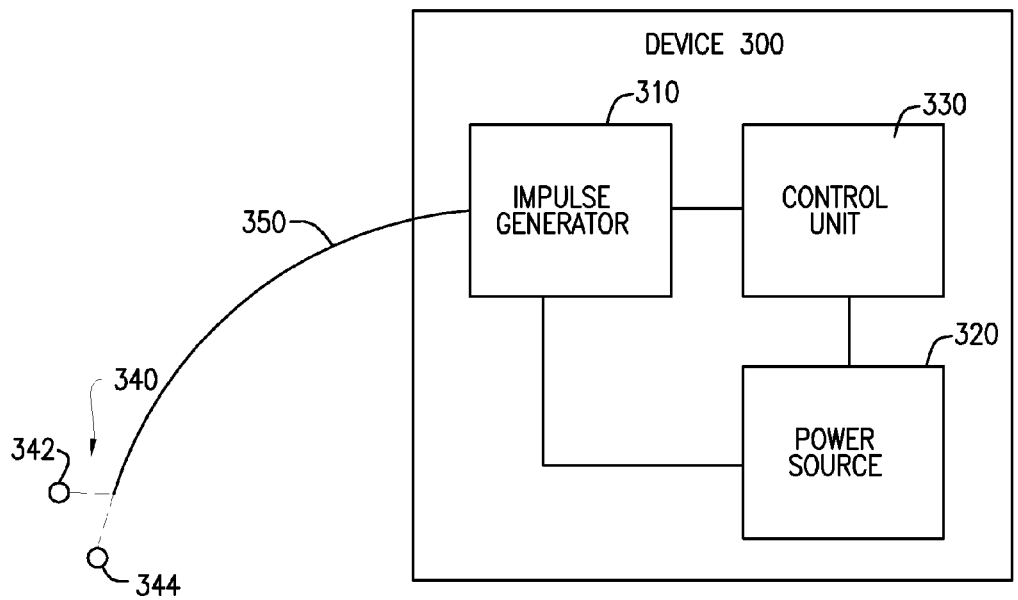
FIG. 1 is a schematic view of a nerve modulating device according to the present invention.

In the present invention, electrical energy is applied through a patient's skin to a target region, such as the carotid sheath or the spinal cord. The invention is particularly useful for applying electrical impulses that interact with the signals of one or more nerves, or muscles, to achieve a therapeutic result, such as relaxation of the smooth muscle of the bronchia, increase in blood pressure associated with orthostatic hypotension, hypertension, treatment of epilepsy, treating ileus conditions, depression, anaphylaxis, obesity, and/or any other ailment affected by nerve transmissions, such as the vagus nerve or the spinal cord. In particular, the present invention can be used to practice the treatments described in the following commonly assigned U.S. Patent Publication Numbers 2009/0183237, 2008/0009913, 2007/0106338, 2007/0106337, and U.S. Pat. Nos. 7,747,324, 7,711,430, 7,725,188, the full disclosures of which are incorporated herein by reference. The disclosures as set for in U.S. Patent Publication Numbers 2009/0157138 and 2008/0183237 are also incorporated herein by reference.

For convenience, the remaining disclosure will be directed specifically to the treatment of acute bronchoconstriction, but it will be appreciated that the systems and methods of the present invention can be applied equally well to other tissues and nerves of the body, including but not limited to other parasympathetic nerves, sympathetic nerves, spinal or cranial nerves, e.g., optic nerve, facial nerves, vestibulocochlear nerves and the like. In addition, the present invention can be applied to treat other symptoms of ailments or the ailments themselves, such as asthma, COPD, sepsis, dialytic hypotension, epilepsy, depression or obesity and other procedures including open procedures, intravascular procedures, interventional cardiology procedures, urology, laparoscopy, general surgery, arthroscopy, thoracoscopy or other cardiac procedures, cosmetic surgery, orthopedics, gynecology, otorhinolaryngology, spinal and neurologic procedures, oncology procedures and the like.

Electrical nerve stimulation is a well known medical treatment used primarily for symptomatic relief and management of chronic intractable pain and as an adjunctive treatment in the management of post surgical and post traumatic acute pain. Electrical nerve stimulation typically involves the application of electrical pulses to the skin of a patient, which pulses are generally of a low frequency and are intended to affect the nervous system in such a way as to suppress the sensation of pain that would indicate acute or chronic injury or otherwise serve as a protective mechanism for the body. Typically, two electrodes are secured to the skin at appropriately selected locations. Mild electrical impulses are then passed into the skin through the electrodes to interact with the nerves lying thereunder. As a symptomatic treatment, nerve stimulation has proven to effectively reduce both chronic and acute pain of patients. However, it has shown no capacity for curing the causes of pain, rather the electrical energy simply interacts with the nervous system to suppress or relieve pain.

The precise mechanisms by which electrical nerve stimulation operates to control pain are not known. When used to treat pain, electrodes are generally attached to the patient in the vicinity of the pain. Thus, for example, in treating joint pain, electrodes would be affixed near the joint and stimulation administered thereto. This localized stimulation then affects the nervous system to reduce the patient's perception of pain, presumably by either affecting the pain signals being sent from the region to the brain or by affecting the brain's perception of the signals it is receiving from the region. Even the body's natural mechanisms for perceiving and affecting pain are poorly understood. However, it is known that various biochemicals are released by nerve and brain cells in response to chemical and/or electrical stimulation of those cells. These neurotransmitters assist in the transmission of electrical messages between and within the peripheral and central nervous systems.

One of the limitations with existing nerve stimulation systems is that the electrical signal is largest near the skin surface and then decays with depth into the tissue. Thus, as the amplitude of the signal is increased, sensory nerves in the skin and nerves innervating superficial muscles are excited first. Before deep excitation can occur, the electrical signal becomes very painful. Thus, existing systems are only capable of stimulating superficial nerves Neurons contain charged ions, including potassium, sodium and chloride. Potassium and sodium are positively charged ions whereas chloride is a negatively charged ion. Unlike most other cells, neurons are able to depolarize, creating a nerve impulse, by rapidly changing the concentration of ions inside the cell relative to the outside of the cell. When at rest, a neuron is polarized, i.e. it has a negative charge on the inside of the cell relative to the outside of the cell. This is because it has a higher concentration of negatively charged ions on the inside. When stimulated, the nerve cell membrane becomes permeable to sodium ions, which rush in temporarily causing a positive charge to build up on the inside relative to the outside. For a short time afterward, referred to as the "refractory period," the nerve cell is unable to "fire" again. A mechanism in its cell membrane has to "pump" the sodium ions back out again, restoring the negative charge and the "action potential" to the cell. Once the action potential is restored the neuron is ready to transmit the next nerve impulse. This all takes place in a very short period of time, measured in milliseconds, as a single nerve cell can fire hundreds of times during a single second.

In the present invention, a deactivating signal is applied to nerve cells which causes the cells to depolarize for the time period that the signal is applied. During this period, the cells are unable to restore the negative charge and thus are unable to transmit nerve impulses. Continuous application of the deactivating signal to the nerves causes the nerves to depolarize for an extended period of time so that the nerves become fatigued or exhausted and unable to polarize while the deactivating electrical impulse is applied. Thus, these nerves become substantially impervious to the activating electrical impulse and will not "fire" or transmit nerve impulses despite the presence of the activating electrical impulse.

FIG. 1 is a schematic diagram of a nerve modulating device 300 for delivering electrical impulses to nerves according to one embodiment of the present invention. As shown, device 300 may include an electrical impulse generator 310; a power source 320 coupled to the electrical impulse generator 310; a control unit 330 in communication with the electrical impulse generator 310 and coupled to the power source 320; and an electrode assembly 340 coupled to the electrical impulse generator 310. As discussed in more detail below, electrode assembly 340 comprises at least one activating electrode 342 and at least one deactivating electrode 344 according to the principles of the present invention. The control unit 330 may control the electrical impulse generator 310 for generation of a signal suitable for amelioration of a patient's condition when the signal is applied via the electrode assembly 340 to the target region of the patient. It is noted that nerve modulating device 300 may be referred to by its function as a pulse generator. U.S. Patent Application Publications 2005/0075701 and 2005/0075702, both to Shafer, both of which are incorporated herein by reference, relating to stimulation of neurons of the sympathetic nervous system to attenuate an immune response, contain descriptions of pulse generators that may be applicable to the present invention.

Figure 2:
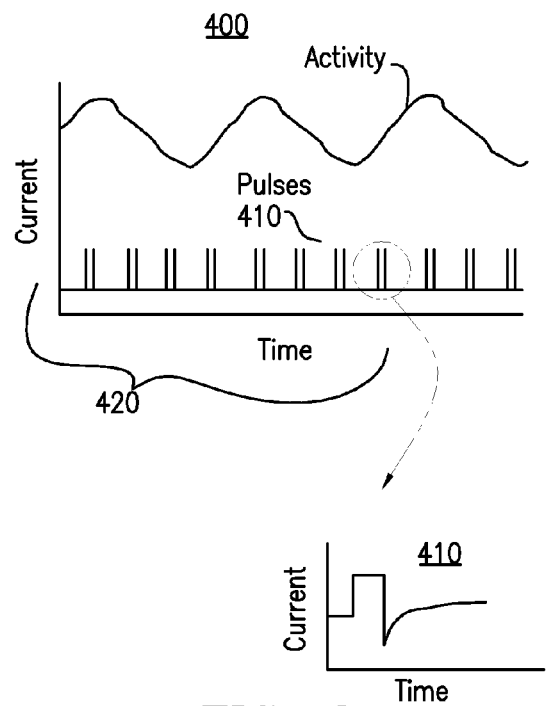
FIG. 2 illustrates an exemplary electrical voltage/current profile for a blocking and/or modulating impulse applied to a portion or portions of a nerve in accordance with an embodiment of the present invention.

FIG. 2 illustrates an exemplary electrical voltage/current profile for a stimulating, blocking and/or modulating impulse applied to a portion or portions of selected nerves in accordance with an embodiment of the present invention. As shown, a suitable electrical voltage/current profile 400 for the blocking and/or modulating impulse 410 to the portion or portions of a nerve may be achieved using pulse generator 310. In a preferred embodiment, the pulse generator 310 may be implemented using a power source 320 and a control unit 330 having, for instance, a processor, a clock, a memory, etc., to produce a pulse train 420 to the electrode(s) 340 that deliver the stimulating, blocking and/or modulating impulse 410 to the nerve(s). Nerve modulating device 300 may be powered and/or recharged from outside the body or may have its own power source 320. By way of example, device 300 may be purchased commercially. Nerve modulating device 300 is preferably programmed with a physician programmer, such as a Model 7432 also available from Medtronic, Inc.

The parameters of the modulation signal 400 are preferably programmable, such as the frequency, amplitude, duty cycle, pulse width, pulse shape, etc. In the case of an implanted pulse generator, programming may take place before or after implantation. For example, an implanted pulse generator may have an external device for communication of settings to the generator. An external communication device may modify the pulse generator programming to improve treatment.

In addition, or as an alternative to the devices to implement the modulation unit for producing the electrical voltage/current profile of the stimulating, blocking and/or modulating impulse to the electrodes, the device disclosed in U.S. Patent Publication No.: 2005/0216062 (the entire disclosure of which is incorporated herein by reference), may be employed. U.S. Patent Publication No.: 2005/0216062 discloses a multi-functional electrical stimulation (ES) system adapted to yield output signals for effecting, electromagnetic or other forms of electrical stimulation for a broad spectrum of different biological and biomedical applications. The system includes an ES signal stage having a selector coupled to a plurality of different signal generators, each producing a signal having a distinct shape such as a sine, a square or a saw-tooth wave, or simple or complex pulse, the parameters of which are adjustable in regard to amplitude, duration, repetition rate and other variables. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated as well as the outputs of various sensors which sense conditions prevailing in this substance whereby the user of the system can manually adjust it or have it automatically adjusted by feedback to provide an electrical stimulation signal of whatever type he wishes and the user can then observe the effect of this signal on a substance being treated.

The treatment impulse signal 410 preferably has a frequency, an amplitude, a duty cycle, a pulse width, a pulse shape, etc. selected to influence the therapeutic result, namely stimulating, blocking and/or modulating some or all of the transmission of the selected nerve. For example the frequency may be about 1 Hz or greater, such as between about 15 Hz to 50 Hz, more preferably around 25 Hz. The modulation signal may have a pulse width selected to influence the therapeutic result, such as about 20 μS or greater, such as about 20 μS to about 1000 μS. The modulation signal may have a peak voltage amplitude selected to influence the therapeutic result, such as about 2 volts or greater, such as about 20 volts to about 200 volts.

The blocking impulse signal will typically have a lower amplitude than the treatment impulse, typically between about 5-50 volts, preferably less than about 2 volts. The blocking impulse will have a frequency that is substantially higher than the treatment impulse, typically at least 2000 Hz and preferably between about 4000 Hz and 5000 Hz and a pulse width that is less than 100 uS.

Figure 3:
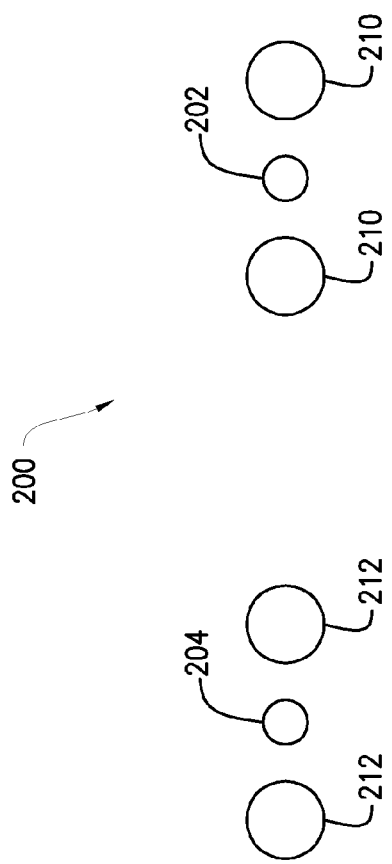
FIG. 3 is a schematic view of an electrode assembly according to one embodiment of the present invention.

Referring now to FIG. 3, an exemplary electrode assembly 200 includes first and second activating electrodes 202, 204 electrically coupled to an impulse generator (not shown) in any suitable manner known in the art. Activating electrodes 202, 204 are preferably surface contact electrodes formed of a suitable material such as conductive silicone, conductive rubber, carbon silicon or metal mesh. A suitable electrode may be formed from Pt-IR (90%/10%), although other materials or combinations or materials may be used, such as platinum, tungsten, gold, stainless steel, copper, palladium, silver, carbon or the like. Electrodes 202, 204 are configured to affix to the skin via a conductive adhesive, tape or gel.

In the preferred embodiment, activating electrodes 202, 204 are separate from each other and spaced from each other a selected distance to ensure that the signal reaches the target region with sufficient energy to stimulate, inhibit or modulate one or more nerves at the target region. The exact distance between activating electrodes will depend on a variety of factors known in the art such as the amplitude and waveform of the impulse delivered to electrodes 202, 204, the size and shape of electrodes 202, 204 and the desired treatment impulse that will be delivered to the target region of the patient. In preferred embodiments, the electrodes are sized, shaped and spaced from each other in such a manner as to deliver the electrical impulse a distance greater than 1 cm from the skin surface, preferably greater than 2 cm and, in some embodiments, greater than 5 cm below the skin surface.

As shown, electrode assembly 200 further includes two pairs of deactivating electrodes 210, 212 coupled to an impulse generator (not shown) in any suitable manner known in the art. Deactivating electrodes 210, 212 are preferably surface contact electrodes having similar characteristics as the activating electrodes 202, 204. As discussed previously, the deactivating electrodes 210, 212 may be coupled to the same impulse generator as activating electrodes or to a different power source. The field of influence around and between the electrodes can be varied by altering the amplitude of the signal(s), the sizes and/or the spacing between electrodes. Therefore, it will be recognized by those skilled in the art that a variety of different embodiments may be used according to the present invention.

As shown, each pair of deactivating electrodes 210, 212 are positioned on either side of one of the activating electrodes 202, 204. Each pair of deactivating electrodes 210, 212 are preferably spaced on either side of each of activating electrodes 202, 204 a selected distance to ensure that the deactivating signal reaches a second target region between the first target region and the outer skin surface. The size and location of the second target region will largely depend on the location of the first target region. For example, if the first target region is about 5 cm below the surface of the patient's skin, the deactivating electrodes will be spaced on either side of each of the activating electrodes such that nerves between the skin surface and up to about 5 cm below are deactivated or depolarized and thus blocked or at least inhibited from stimulation by the activating electrodes. This allows treatment of deeper tissue without stimulation of shallow nerves, which would otherwise cause the patient pain.

Figure 4:
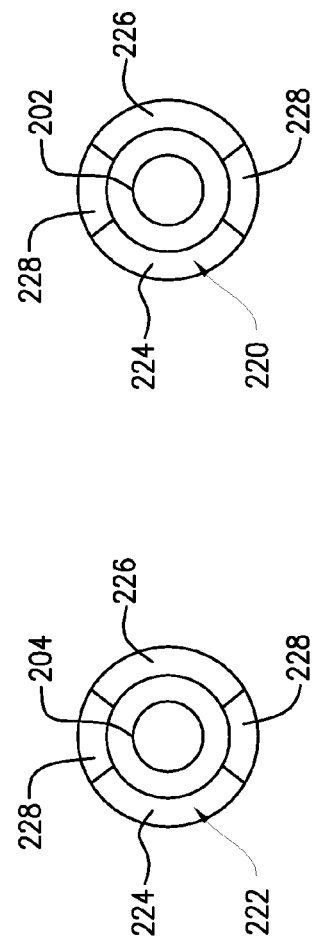
FIG. 4 is a schematic view of an alternative embodiment of an electrode assembly according to the present invention.

FIG. 4 is a schematic view of an alternative embodiment of electrode assembly 200. As shown, electrode assembly 200 comprises activating electrodes 202, 204 and deactivating electrodes 220, 222. Deactivating electrodes 220, 222 are annular electrodes each having an anode 224 and a cathode 226 separated from each other by an insulator 228. Alternatively, the electrode assembly may include separate return electrodes (not shown) in which case the annular electrodes may be a single electrode (i.e. without an insulator) Deactivating electrodes 220, 222 are configured for placement around activating electrodes 202, 204. Preferably, the deactivating electrodes will have an inner diameter that allows for suitable spacing between activating electrodes 202, 204 and the inner surface 224 of deactivating electrodes, 220, 222. Similar to the previous embodiment, the exact spacing will depend on the location of the first target region.

FIGS. 5 and 6 illustrate an exemplary electric field profile for the electrode assembly of FIG. 3. In this example, the activating and deactivating signals are designed to deactivate nerves at a depth of around 0.5 cm below the surface of the skin, while allowing nerve stimulation at a depth of around 5.0 cm below the surface of the skin. FIG. 5 illustrates the activating and deactivating signals as a function of distance along the nerve axis at a depth of 0.5 cm from the surface of the skin. The solid trace is the signal that inactivates nerve transmission while the dotted trace is the signal that stimulates nerve transmission. In the presence of the inactivating signal, nerve transmission cannot be activated by any signal at the depth of 0.5 cm. Thus, the activating signal passes right through the nerves at this depth without causing any stimulation, thereby minimizing any sensations felt by the patient at this depth.

FIG. 6 illustrates the activating and deactivating signals as a function of distance along the nerve axis at a depth of 5.0 cm from the surface of the skin. Again, the solid trace is the signal that inactivates nerve transmissions while the dotted trace is the signal that stimulates nerve transmissions. In this profile, the inactivating signal is below its inactivating threshold allowing the activating signal to stimulate action potentials at the depth of 5.0 cm. Thus, the activating signal causes nerve stimulation at this depth.

In a preferred embodiment of the invention, a method of treating bronchial constriction comprises applying one or more electrical impulse(s) of a frequency of about 15 Hz to 50 Hz to a selected region of the carotid sheath to reduce a magnitude of constriction of bronchial smooth muscle. As discussed in more detail below, applicant has made the unexpected discovered that applying an electrical impulse to a selected region of the carotid sheath within this particular frequency range results in almost immediate and significant improvement in bronchodilation, as discussed in further detail below. Applicant has further discovered that applying electrical impulses outside of the selected frequency range (15 Hz to 50 Hz) does not result in immediate and significant improvement in bronchodilation. Preferably, the frequency is about 25 Hz. In this embodiment, the electrical impulse(s) are of an amplitude of between about 0.75 to 12 volts (depending on the size and shape of the electrodes and the distance between the electrodes and the selected nerve(s)) and have a pulsed on-time of between about 50 to 500 microseconds, preferably about 200-400 microseconds.

Figure 7:
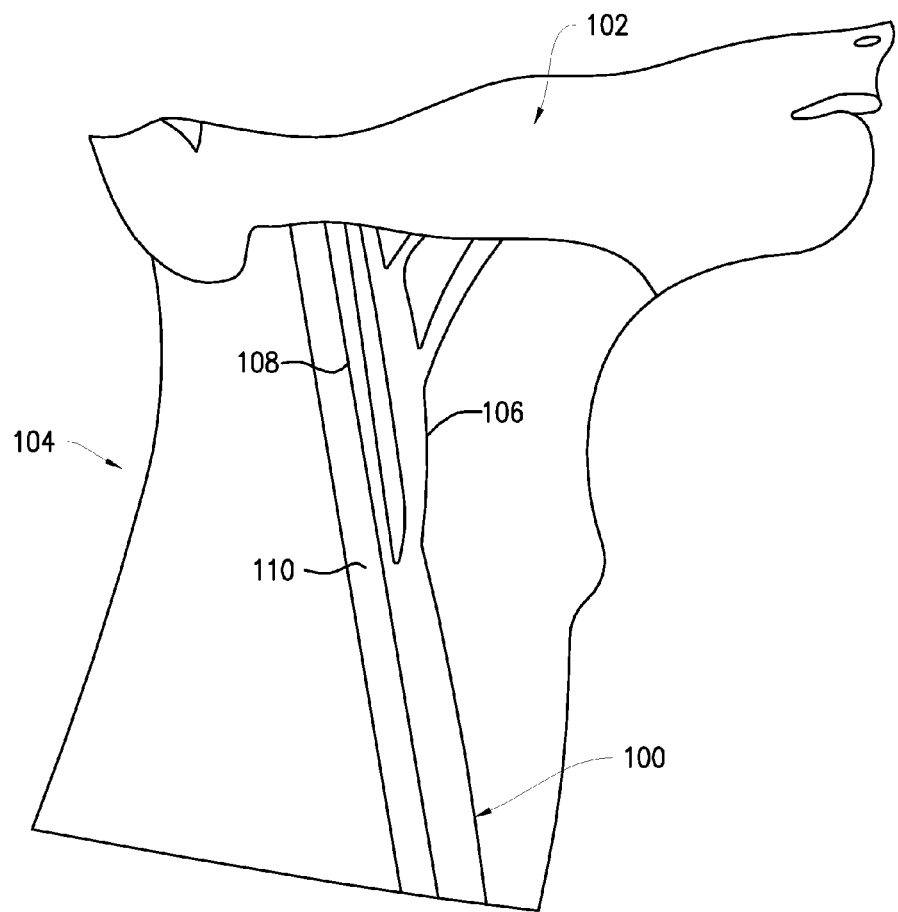
FIG. 7 illustrates the major vessels of the neck, including the carotid sheath.

FIG. 7 illustrates some of the major structures of the neck. As shown, the common carotid artery 100 extends from the base of the skull 102 through the neck 104 to the first rib and sternum (not shown). Carotid artery 100 includes an external carotid artery 106 and an internal carotid artery 108 and is protected by fibrous connective tissue called the carotid sheath. The carotid sheath is located at the lateral boundary of the retopharyngeal space at the level of the oropharynx on each side of the neck 104 and deep to the sternocleidomastoid muscle. The three major structures within the carotid sheath are the common carotid artery 100, the internal jugular vein 110 and the vagus nerve (not shown). The carotid artery lies medial to the internal jugular vein and the vagus nerve is situated posteriorly between the two vessels.

Figure 8:
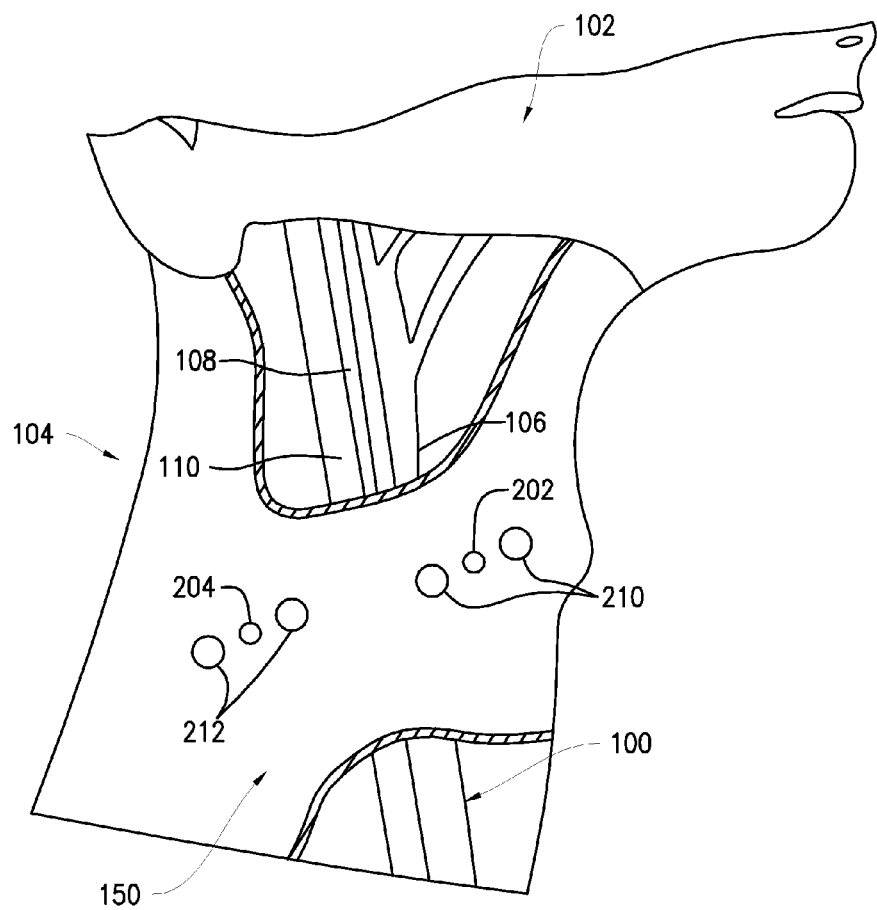
FIG. 8 illustrates the electrode assembly of FIG. 3 in use on a patient's neck for applying an electrical impulse in or around the carotid sheath of the patient.

FIG. 8 illustrates a method according to the present invention of applying an electrical impulse to the region around the carotid sheath. As shown, activating electrodes 202, 204 are surface contact electrodes that are placed in electrical contact with the outer skin surface 150 of a patient's neck. Activating electrodes 202, 204 are coupled to a power source in any suitable manner (e.g., through leads that are not shown in FIG. 8). Electrodes 202, 204 are positioned such that an electrical impulse applied thereto will pass through the skin surface 150 to a target region adjacent to or within the carotid sheath. The carotid sheath is approximately 2-5 cm beneath the surface of the patient's skin. Thus, electrodes 202, 204 will preferably be spaced from each other to allow for a suitable electrical impulse to pass through to a depth of 2-5 cm under skin surface 150.

Deactivating electrodes 210, 212 are two pairs of surface contact electrodes positioned in electrical contact with skin surface 150 around the activating electrodes 202, 204. Deactivating electrodes 210, 212 are also coupled to a power source in any suitable manner known in the art. An electrical impulse is applied to each pair of deactivating electrodes 210, 212 such that an electrical impulse applied thereto will pass through the patient's skin surface 150 to the region between the target region at the carotid sheath and the skin surface 150. As discussed previously, the electrical impulse applied to deactivating electrodes 210, 212 is configured to depolarize and fatigue the superficial nerves. In this manner, the electrical impulse applied to activating electrodes 202, 204 will not stimulate the superficial nerves; allowing this impulse to be applied through the superficial nerves to the carotid sheath.

Figure 9:
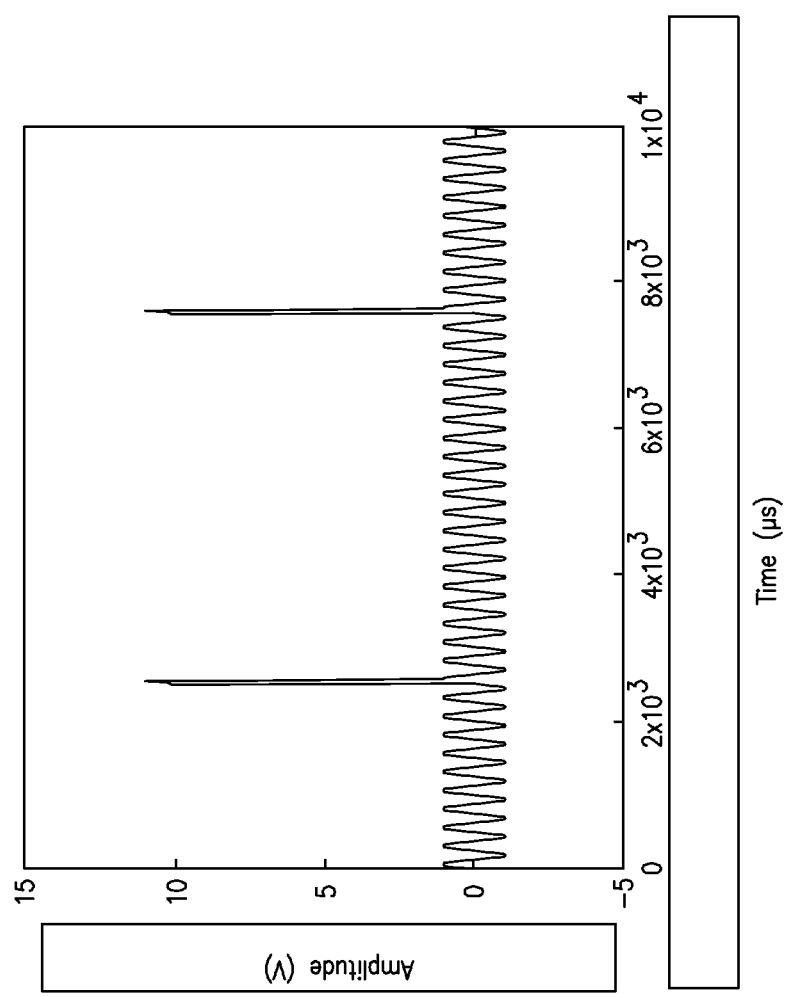
FIG. 9 illustrates an amplitude profile of an alternative embodiment of the invention.

FIG. 9 illustrates an amplitude profile for an alternative embodiment of the invention. In this embodiment, a source of electrical energy, such as a pulse generator, delivers two signals of different amplitudes to one set of contact electrodes. As in the previous embodiments, the electrodes are preferably surface contact electrodes designed for use on the outer skin surface of a patient. The electrodes may have bipolar or monopolar configurations. As shown, a relatively high amplitude signal (e.g., about 20-200 volts) is used as the treatment signal for modulating nerves at the target region within the patient. A blocking impulse is also applied to the electrodes. The blocking signal has a voltage in the range of about 5-50 volts and a frequency selected to deactivate nerves at a second target region between the outer skin surface of the patient and the first deeper target region of the treatment signal. Typically, the frequency of the blocking signal is about 4K Hz to about 5K Hz. In this manner, the treatment signal does not cause stimulation to the nerves within the second target region. The relative amplitudes of the two signals in this embodiment will, of course, depend on the depth of the target region selected for modulation.

In one specific embodiment, method and devices of the present invention are particularly useful for providing substantially immediate relief of acute symptoms associated with bronchial constriction such as asthma attacks, COPD exacerbations and/or anaphylactic reactions. One of the key advantages of the present invention is the ability to provide almost immediate dilation of the bronchial smooth muscle in patients suffering from acute bronchoconstriction, opening the patient's airways and allowing them to breathe and more quickly recover from an acute episode (i.e., a relatively rapid onset of symptoms that are typically not prolonged or chronic).

The magnitude of bronchial constriction in a patient is typically expressed in a measurement referred to as the Forced Expiratory Volume in 1 second ($FEV_1$). $FEV_1$ represents the amount of air a patient exhales (expressed in liters) in the first second of a pulmonary function test, which is typically performed with a spirometer. The spirometer compares the $FEV_1$ result to a standard for the patient, which is based on the predicted value for the patient's weight, height, sex, age and race. This comparison is then expressed as a percentage of the $FEV_1$ as predicted. Thus, if the volume of air exhaled by a patient in the first second is 60% of the predicted value based on the standard, the $FEV_1$ will be expressed in both the actual liters exhaled and as a percentage of predicted (i.e., 60% of predicted).

Applicants have disclosed a system and method for increasing a patient's $FEV_1$ in a relatively short period of time. Preferably, the electrical impulse applied to the patient is sufficient to increase the $FEV_1$ of the patient by a clinically significant amount in a period of time less than about 6 hours, preferably less than 3 hours and more preferably less than 90 minutes. In an exemplary embodiment, the clinically significant increase in $FEV_1$ occurs in less than 15 minutes. A clinically significant amount is defined herein as at least a 12% increase in the patient's $FEV_1$ versus the $FEV_1$ prior to application of the electrical impulse.

A general approach to treating bronchial constriction in accordance with one or more embodiments of the invention may include a method of (or apparatus for) treating bronchial constriction associated with anaphylactic shock, COPD or asthma, comprising applying at least one electrical impulse to one or more selected nerve fibers of a mammal in need of relief of bronchial constriction. The method may include: positioning an electrode assembly on the surface of the patient's neck near or adjacent to target region around the carotid sheath; applying a deactivating electrical impulse to the electrode assembly to deactivate nerves located between the skin surface and the target region and then applying an activating electrical impulse configured to modulate one or more nerves at the target region, wherein the activating electrical impulse is of a frequency between about 15 Hz to 50 Hz.

The activating electrical impulse may be of an amplitude of between about 2-200 volts, depending on the size and shape of the activating electrodes and the distance between these electrodes and the selected nerve fibers. The activating electrical impulse may be one or more of a full or partial sinusoid, square wave, rectangular wave, and/or triangle wave and it may have a pulsed on-time of between about 50 to 500 microseconds, such as about 100, 200 or 400 microseconds. The polarity of the pulses may be maintained either positive or negative. Alternatively, the polarity of the pulses may be positive for some periods of the wave and negative for some other periods of the wave. By way of example, the polarity of the pulses may be altered about every second.

While the exact physiological causes of asthma, COPD and anaphylaxis have not been determined, the present invention postulates that the direct mediation of the smooth muscles of the bronchia is the result of activity in one or more nerves near or in the carotid sheath. In the case of asthma, it appears that the airway tissue has both (i) a hypersensitivity to the allergen that causes the overproduction of the cytokines that stimulate the cholinergic receptors of the nerves and/or (ii) a baseline high parasympathetic tone or a high ramp up to a strong parasympathetic tone when confronted with any level of cholenergic cytokine. The combination can be lethal. Anaphylaxis appears to be mediated predominantly by the hypersensitivity to an allergen causing the massive overproduction of cholenergic receptor activating cytokines that overdrive the otherwise normally operating vagus nerve to signal massive constriction of the airways. Drugs such as epinephrine drive heart rate up while also relaxing the bronchial muscles, effecting temporary relief of symptoms from these conditions. Experience has shown that severing the vagus nerve (an extreme version of reducing the parasympathetic tone) has an effect similar to that of epinephrine on heart rate and bronchial diameter in that the heart begins to race (tachycardia) and the bronchial passageways dilate.

In accordance with the present invention, the delivery, in a patient suffering from severe asthma, COPD or anaphylactic shock, of an electrical impulse sufficient to stimulate, block and/or modulate transmission of signals will result in relaxation of the bronchi smooth muscle, dilating airways and/or counteract the effect of histamine on the vagus nerve. Depending on the placement of the impulse, the stimulating, blocking and/or modulating signal can also raise the heart function.

Stimulating, blocking and/or modulating the signal in selected nerves in or around the carotid sheath to reduce parasympathetic tone provides an immediate emergency response, much like a defibrillator, in situations of severe asthma or COPD attacks or anaphylactic shock, providing immediate temporary dilation of the airways and optionally an increase of heart function until subsequent measures, such as administration of epinephrine, rescue breathing and intubation can be employed. Moreover, the teachings of the present invention permit immediate airway dilation and/or heart function increase to enable subsequent life saving measures that otherwise would be ineffective or impossible due to severe constriction or other physiological effects. Treatment in accordance with the present invention provides bronchodilation and optionally increased heart function for a long enough period of time so that administered medication such as epinephrine has time to take effect before the patient suffocates.

In a preferred embodiment, a method of treating bronchial constriction comprises stimulating selected nerve fibers responsible for reducing the magnitude of constriction of smooth bronchial muscle to increase the activity of the selected nerve fibers. Certain signals of the parasympathetic nerve fibers cause a constriction of the smooth muscle surrounding the bronchial passages, while other signals of the parasympathetic nerve fibers carry the opposing signals that tend to open the bronchial passages. Specifically, it should be recognized that certain signals, such as cholinergic fibers mediate a response similar to that of histamine, while other signals (e.g., inhibitory nonadrenergic, noncholinergic or iNANC nerve fibers) generate an effect similar to epinephrine. Given the postulated balance between these signals, stimulating the iNANC nerve fibers and/or blocking or removing the cholinergic signals should create an imbalance emphasizing bronchodilation.

In one embodiment of the present invention, the selected nerve fibers are inhibitory nonadrenergic noncholinergic (iNANC) nerve fibers which are generally responsible for bronchodilation. Stimulation of these iNANC fibers increases their activity, thereby increasing bronchodilation and facilitating opening of the airways of the mammal. The stimulation may occur through direct stimulation of the efferent iNANC fibers that cause bronchodilation or indirectly through stimulation of the afferent sympathetic or parasympathetic nerves which carry signals to the brain and then back down through the iNANC nerve fibers to the bronchial passages.

In certain embodiments, the iNANC nerve fibers are associated with the vagus nerve and are thus directly responsible for bronchodilation. Alternatively, the iNANC fibers may be interneurons that are completely contained within the walls of the bronchial airways or extend from the esophagus to the trachea. These interneurons are responsible for modulating the cholinergic nerves in the bronchial passages. In this embodiment, the increased activity of the iNANC interneurons will cause inhibition or blocking of the cholinergic nerves responsible for bronchial constriction, thereby facilitating opening of the airways.

As discussed above, certain parasympathetic signals mediate a response similar to histamine, thereby causing a constriction of the smooth muscle surrounding the bronchial passages. Accordingly, the stimulating step of the present invention is preferably carried out without substantially stimulating the parasympathetic nerve fibers, such as the cholinergic nerve fibers associated with the vagus nerve, that are responsible for increasing the magnitude of constriction of smooth muscle. In this manner, the activity of the iNANC nerve fibers are increased without increasing the activity of the adrenergic fibers which would otherwise induce further constriction of the smooth muscle. Alternatively, the method may comprise the step of actually inhibiting or blocking these cholinergic nerve fibers such that the nerves responsible for bronchodilation are stimulated while the nerves responsible for bronchial constriction are inhibited or completely blocked. This blocking signal may be separately applied to the inhibitory nerves; or it may be part of the same signal that is applied to the iNANC nerve fibers.

While it is believed that there are little to no direct sympathetic innervations of the bronchial smooth muscle in most individuals, recent evidence has suggested asthma patients do have such sympathetic innervations within the bronchial smooth muscle. In addition, the sympathetic nerves may have an indirect effect on the bronchial smooth muscle. Accordingly, alternative embodiments of the prevent invention contemplate a method of stimulating selected efferent sympathetic nerves responsible for mediating bronchial passages either directly or indirectly. The selected efferent sympathetic nerves may be nerves that directly innervate the smooth muscles, nerves that release systemic bronchodilators or nerves that directly modulate parasympathetic ganglia transmission (by stimulation or inhibition of preganglionic to postganglionic transmissions).

In another embodiment of the present invention, a method for acutely treating post-operative ileus by applying one or more electrical impulses in or around the spinal cord is described. Ileus occurs from hypomotility of the gastrointestinal tract in the absence of a mechanical bowel obstruction. This suggests that the muscle of the bowel wall is transiently impaired and fails to transport intestinal contents. This lack of coordinated propulsive action leads to the accumulation of both gas and fluids within the bowel. Although ileus has numerous causes, the postoperative state is the most common scenario for ileus development. Frequently, ileus occurs after intraperitoneal operations, but it may also occur after retroperitoneal and extra-abdominal surgery. The longest duration of ileus has been reported to occur after colonic surgery.

In accordance with this embodiment, methods and apparatus for treating the temporary arrest of intestinal peristalsis provide for: inducing at least one of an electric current, an electric field and an electromagnetic field in or around the spinal cord to modulate, stimulate and/or block nerve signals thereof such that intestinal peristalsis function is at least partially improved. Specifically, prior to, during or after the operation that causes ileus, an electrode assembly is positioned on the patient's outer skin surface in the vicinity of the target region within the spinal cord of a patient. In preferred embodiments, the electrical impulse is applied to at least a portion of the splanchnici nerves of the sympathetic nerve chain, and/or the spinal levels from T5 to L2. As discussed above, a deactivating signal is applied to deactivate the nerves located between the skin surface and the target region. An activating electrical impulse is then produced from a source of electrical energy to deliver one or more electrical impulses sufficient to modulate, stimulate and/or block nerve signals thereof such that intestinal peristalsis function is improved.

The drive signals inducing the current and/or fields preferably have a frequency, an amplitude, a duty cycle, a pulse width, a pulse shape, etc. selected to influence the therapeutic result, namely modulating some or all of the nerve transmissions in and around the target region. By way of example, the parameters of the drive signal may include a sine wave profile having a frequency of about 10 Hz or greater, such as between about 10-200 Hz, between about 15 Hz to 120 Hz, between about 25 Hz to about 50 Hz, between about 40-65 Hz, and more preferably about 50 Hz. The drive signal may include a duty cycle of between about 1 to 100%. The drive signal may have a pulse width selected to influence the therapeutic result, such as about 20 us or greater, such as about 20 us to about 1000 us. The drive signal may have a peak voltage amplitude selected to influence the therapeutic result, such as about 2 volts or greater, such as about 20 volts to about 200 volts. The electric or electromagnetic field may be administered for a predetermined duration, such as between about 5 minutes and about 1 hour, or between about 5 minutes and about 24 hours. A more complete description of the mechanisms for increasing motility can be found in commonly assigned co-pending U.S. patent application Ser. No. 12/246,605, which has previously been incorporated herein by reference.

In yet another embodiment, the present invention can be used for treatment of hypotension utilizing an electrical signal that may be applied to selected nerves in the carotid sheath, such as the vagus nerve, to temporarily stimulate, block and/or modulate the signals in the selected nerves. The present invention also encompasses treatment of pathologies causing hypotension, both chronic and acute hypotension, such as in patients with thyroid pathologies and those suffering from septic shock. This treatment of hypotension may accompany treatment for other conditions, such as bronchial constriction, that also may occur in situations of shock.

In this embodiment, the present invention contemplates an electrical assembly that can be positioned on the outer surface of the patient's neck adjacent a target region in or around the carotid sheath (as described above). A deactivating signal is applied to the electrode assembly to deactivate nerves between the skin surface and the target region and an activating electrical impulse is applied to at least one selected region of the carotid sheath to stimulate, block and/or modulate signals to the smooth muscle surrounding blood vessels, causing them to constrict and raise blood pressure.

Although the invention is not limited by any theory of operation, in one or more embodiments of the present invention, it is believed that the impulses may be applied in such a manner that the myocardium is relaxed to reduce the baseline level of tonic contraction, vasoconstriction occurs to increase blood pressure, and/or in cases of some shock, the smooth muscle lining the bronchial passages is relaxed to relieve the spasms that occur, such as during anaphylactic shock. The electric field generated around the active and return electrodes creates a field of effect that permeates the target nerve fibers and causes the stimulating, blocking and/or modulating of signals to the subject muscles. A more complete description of the mechanisms for elevating blood pressure can be found in commonly assigned co-pending U.S. patent application Ser. No. 11/592,095, which has previously been incorporated herein by reference.

In yet another embodiment, the present invention can be used for the treatment of hypertension by stimulating one or more baroreceptor nerve(s) in a patient. Baroreceptors are sensors located in blood vessels that detect the pressure of blood flowing through them. Baroreceptors can send messages to the central nervous system to increase or decrease total peripheral resistance and cardiac output. Baroreceptors act immediately as part of a negative feedback system called the baroreflex, as soon as there is a change from the usual blood pressure mean arterial blood pressure, returning the pressure to a normal level. They are an example of a short term blood pressure regulation mechanism. Baroreceptors detect the amount of stretch of the blood vessel walls, and send the signal to the nervous system in response to this stretch. A change in the mean arterial pressure induces depolarisation of these sensory endings which results in action potentials. These action potentials are conducted to the central nervous system by axons and have a direct effect on the cardiovascular system through autonomic neurons.

In some patients with hypertension, the baroreceptors are functioning, but they have become stiff or non-responsive and therefore do not activate the appropriate signal in response to high blood pressure. In this embodiment, an electrical impulse is applied to one or more surface contact electrodes preferably in or around the patient's neck. The electrical impulse is sufficient to stimulate the baroreceptors and cause them to send the appropriate signal to the nervous system, thereby reducing the patient's blood pressure. In a preferred embodiment, the electrical impulse has a frequency of between about 20 Hz to 300 Hz, preferably between about 75 Hz to 100 Hz and about 100 Hz in an exemplary embodiment. The amplitude of the electrical impulse will be sufficient for the impulse to be applied from the surface of the patient's skin.

In this embodiment, the nerves located between the target baroreceptors and the patient's skin surface are deactivated by a second electrical impulse according to the principles described above. This allows the first stimulating signal to be applied to the baroreceptors from the surface of the patient's skin without stimulating the superficial nerves. The second electrical impulse may be applied to the same surface contact electrodes, or to a second set of deactivating electrodes as already described.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for treating hypotension comprising:
   contacting an activating device to a first outer skin surface of a patient;
   contacting a deactivating device to a second outer skin surface of the patient;
   applying a first electrical impulse with a first frequency to the activating device such that the first electrical impulse modulates at least one target nerve in a selected first region of a carotid sheath of the patient in need of relief from hypotension, such that increased blood pressure is achieved; and
   applying a second electrical impulse with a second frequency different than the first frequency to the deactivating device such that the second electrical impulse substantially blocks the first electrical impulse from modulating nerves in a second region between the outer skin surface and the selected first region of the carotid sheath.

2. The method of claim 1, wherein increased blood pressure is achieved by at least one of improving myocardium performance and controlling vasoconstriction.

3. The method of claim 1, wherein second electrical impulse deactivates one or more nerves located between the outer skin surface and the selected first region of the carotid sheath.

4. The method of claim 1, wherein the activating device and the deactivating device are a same device.

5. The method of claim 1, wherein the first outer skin surface and second outer skin surface are adjacent locations at the outer skin surface.

6. The method of claim 1, wherein the first outer skin surface and second outer skin surface are a same general location at the outer skin surface.

7. A method for treating bronchoconstriction comprising:
   contacting an activating device to a first outer skin surface of a patient;
   contacting a deactivating device to a second outer skin surface of the patient;
   applying a first electrical impulse with a first frequency to the activating
   device such that the first electrical impulse modulates at least one target nerve in a selected first region of the carotid sheath of the patient in need of relief from bronchial smooth muscle constriction wherein the magnitude of constriction is reduced; and
   applying a second electrical impulse with a second frequency different than the first frequency to the deactivating device such that the second electrical impulse substantially blocks the first electrical impulse from modulating nerves in a
   second region between the outer skin surface and the selected first region of the carotid sheath.

8. The method of claim 7, wherein the second electrical impulse deactivates one or more nerves located between the outer skin surface and the selected first region of the carotid sheath.

9. The method of claim 7, wherein the activating device and the deactivating device are a same device.

10. The method of claim 7, wherein the first outer skin surface and second outer skin surface are adjacent locations at the outer skin surface.

11. The method of claim 7, wherein the first outer skin surface and second outer skin surface are a same general location at the outer skin surface.

* * * * *